United States Patent [19]

McMillin

[11] Patent Number: 5,294,391
[45] Date of Patent: Mar. 15, 1994

[54] METHOD OF MAKING A FIBER REINFORCED COMPOSITE STRUCTURE INCLUDING RANDOMIZING THE REINFORCING FIBERS

[75] Inventor: Carl R. McMillin, Brecksville, Ohio

[73] Assignee: AcroMed Corporation, Cleveland, Ohio

[21] Appl. No.: 9,292

[22] Filed: Jan. 26, 1993

Related U.S. Application Data

[62] Division of Ser. No. 709,379, Jun. 3, 1991.

[51] Int. Cl.$^5$ .............................................. B29C 67/14
[52] U.S. Cl. ...................................... 264/103; 28/103; 156/148; 156/309.6; 264/138; 264/257
[58] Field of Search ............... 264/103, 257, 258, 248, 264/138; 156/148, 309.6; 28/101, 102, 103

[56] References Cited

U.S. PATENT DOCUMENTS

| | | | |
|---|---|---|---|
| 3,560,326 | 2/1971 | Bunting, Jr. et al. | 28/103 |
| 3,775,209 | 11/1973 | Paquette et al. | 28/103 |
| 3,999,971 | 12/1976 | Drummond | 28/103 |
| 4,542,060 | 9/1985 | Yoshida et al. | 28/103 |
| 4,871,491 | 10/1989 | McMahon et al. | 264/257 |
| 4,916,997 | 4/1990 | Spain | 156/148 |
| 4,925,729 | 5/1990 | O'Conner | 156/148 |
| 4,950,439 | 8/1990 | Smith et al. | 264/257 |
| 5,139,593 | 8/1992 | Loubineux et al. | 264/257 |

FOREIGN PATENT DOCUMENTS 2096195A 10/1982 United Kingdom ............... 264/257

*Primary Examiner*—Jay H. Woo
*Assistant Examiner*—Robert B. Davis
*Attorney, Agent, or Firm*—Tarolli, Sundheim & Covell

[57] ABSTRACT

A method of forming a three-dimensional fiber reinforced composite structure includes comprises the steps of providing yarn made of a plurality of continuous reinforcing fibers and fibers which when melted form a matrix material, randomizing the yarn, forming the randomized yarn into a preform, and consolidating the preform in one direction. Each of the plurality of reinforcing fibers extends continuously and randomly throughout the matrix because of the randomizing. The fiber reinforced composite structure formed by the present method is particularly suitable for manufacturing a vertebral prosthetic spinal implant device.

17 Claims, 2 Drawing Sheets

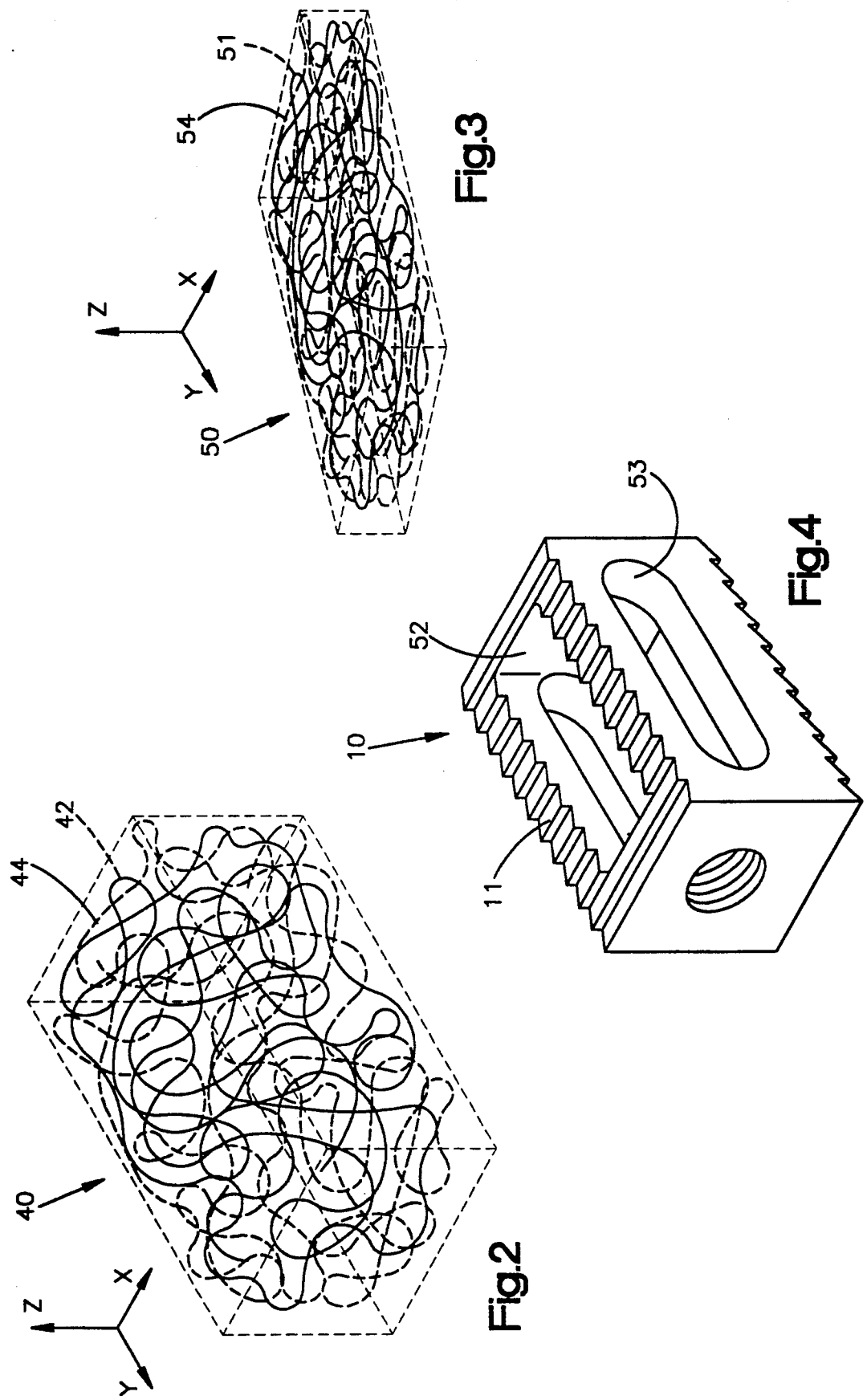

METHOD OF MAKING A FIBER REINFORCED COMPOSITE STRUCTURE INCLUDING RANDOMIZING THE REINFORCING FIBERS

This is a divisional of co-pending application Ser. No. 709,379 filed on Jun. 3, 1991.

TECHNICAL FIELD

The present invention relates to a fiber reinforced composite structure, and is particularly directed to a structure comprising a matrix material which is fiber reinforced and a method of making the structure.

BACKGROUND ART

There are many known composite structures which comprise a fiber reinforced matrix material. A known fiber reinforced composite structure comprises a matrix material having chopped pieces of fiber dispersed therein. The chopped pieces of fiber are typically randomly located or semi-aligned in the matrix material.

Another known fiber reinforced composite structure comprises a laminated stack of layers of a matrix material containing linearly oriented fibers. The fibers within each layer have only one direction of orientation. However, the direction of orientation of the fibers in one layer may be at a different angle relative to the direction of orientation of the fibers in an adjacent layer.

A disadvantage of a laminated stack of layers of a matrix material containing linearly oriented fibers is that there is no fiber reinforcement in a direction perpendicular to the layers. A known way to strengthen the fibers in the direction perpendicular to the layers is to stitch the layers together. A disadvantage in stitching the layers together is that the stitching process is labor and equipment intensive.

Also, known fiber reinforced composite structures are made from knitted fibers and woven fibers which form a three-dimensional structure. However, the making of these composite structures is also labor and equipment intensive.

SUMMARY OF THE INVENTION

In accordance with the present invention, a fiber reinforced composite structure is made by a method which comprises the steps of providing a length of yarn made of fibers which are to become a matrix material and of a plurality of matrix material reinforcing fibers. Each of the reinforcing fibers and the fibers which are to become the matrix material has a length equal to the length of the yarn. The yarn is randomized by causing the fibers of the yarn to interlocks, intertwine and tangle with each other. Each fiber of the yarn also interlocks, intertwines and tangles with itself. Preferably, the step of randomizing is performed by hooking the yarn with a hook and moving the hook to cause the fibers to extend randomly, interlock, intertwine, and tangle with other fibers and themselves.

The randomized yarn is formed into a preform, and the preform is consolidated in one direction. As the preform is consolidated, it is heated to a temperature at which the fibers which are to become the matrix material melt but the reinforcing fibers do not melt. As a result of consolidating and heating the preform, the majority of the reinforcing fibers lie substantially parallel with a plane extending in X and Y directions and portions of the reinforcing fibers also lie transverse to the plane to highly interlock the reinforcing fibers. The reinforcing fibers remain interlocked, intertwined, and tangled, and extend randomly throughout the matrix material formed by the melted fibers. After consolidating and heating the preform, the body of material is cooled so that a device such as a vertebral prosthetic spinal implant device can be machined from the body of material.

The vertebral prosthetic spinal implant device comprises a body insertable into a channel formed in the face of vertebra. The body includes peripheral surfaces for engaging parts of the vertebra. The body is made of a matrix of a first material and a plurality of reinforcing fibers of a second material in the matrix. Each of the plurality of reinforcing fibers has fiber portions randomly disposed in X-Y plane and fiber portions which weave through the X-Y plane in a Z direction. The fiber portions of one reinforcing fiber interlock, intertwine, and tangle with the fiber portions of another reinforcing fiber and with fiber portions of itself to reinforce the body.

BRIEF DESCRIPTION OF THE DRAWINGS

The foregoing and other features of the present invention will become apparent to one skilled in the art upon a consideration of the following description of the invention with reference to the accompanying drawings, wherein:

FIG. 2 is a schematic perspective view of a preform used in the method of FIG. 1 but illustrating only two of many fibers forming the preform;

FIG. 3 is a schematic perspective view of a composite structure made by the method steps shown in the flow chart of FIG. 1 but illustrating only two of many reinforcing fibers in the composite structure; and FIG. 4 is a schematic perspective view of a vertebral prosthetic implant device made of the composite structure of FIG. 3.

DESCRIPTION OF THE PREFERRED EMBODIMENTS

Figure 1:
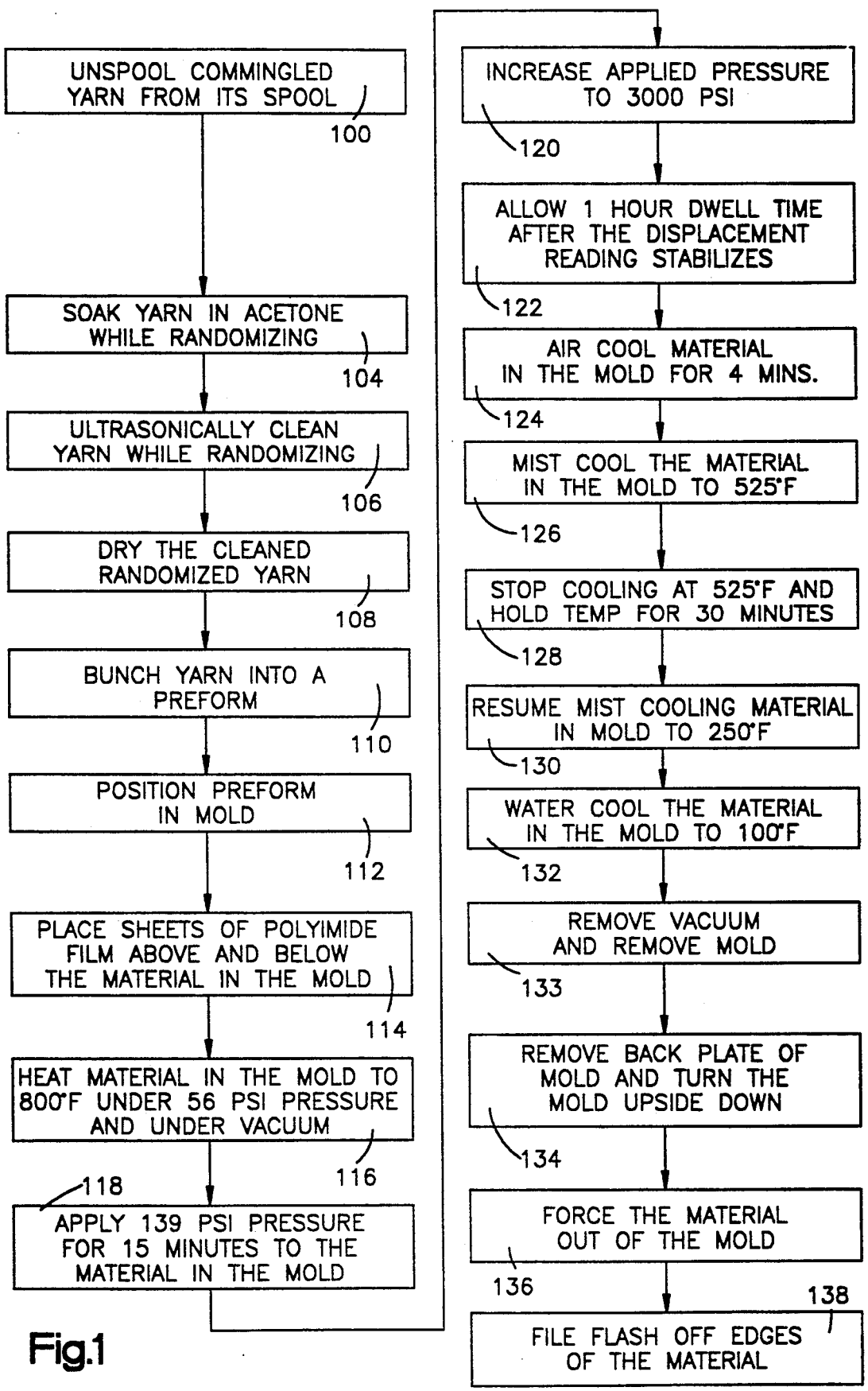
FIG. 1 is a flow chart of method steps to be followed in making a three-dimensional fiber reinforced composite structure in accordance with the present invention.

The present invention is directed to a fiber reinforced composite structure and a method of making the structure. The specific construction and use of the fiber reinforced composite structure may vary as will be understood from the description below.

Referring to FIG. 1, a flow chart is depicted illustrating a method of making a fiber reinforced composite structure constructed in accordance with the present invention. In step 100, a continuous piece of yarn wrapped around a spool is unspooled until the desired weight of yarn is unspooled. As the yarn is unspooled, fibers of the yarn may be spread apart such as by a comb, a roller, an air blast, or the like. The unspooled continuous piece of yarn has two ends and a length. The yarn consists of (i) continuous reinforcing fibers having a length equal to the length of the piece of yarn, and (ii) fibers, also having a length equal to the length of the piece of yarn, which when melted form a matrix material which is reinforced by the continuous reinforcing fibers.

Preferably, the yarn is a commingled yarn known as Ultrapek PEKEKK manufactured by BASF Structural materials, Inc., Charlotte, N.C. Ultrapek PEKEKK comprises continuous carbon fibers commingled with continuous polymer fibers. The continuous carbon fibers are the reinforcing fibers and the continuous polymer fibers are the fibers which when melted become the matrix material. Ultrapek PEKEKK has a total crystallinity content of 10 to 25 percent and has outstanding solvent resistance properties. A typical commingled yarn consisting of Ultrapek PEKEKK has approximately a density of 0.058 lbs./in$^3$, a total denier of 2,750 gm/9,000 m, a fiber area of $2.96 \times 10^{-4}$ in$^2$, and a yield of 1,590 yd/lb.

In one embodiment of the present invention, the material of which the yarn is made is continuous carbon fibers commingled with continuous polymer fibers as in the case of Ultrapek PEKEKK described hereinabove. In another embodiment of the present invention, the material of which the yarn is made may be continuous carbon fibers that have firmly adhering polymer powder bonded to the carbon fibers. Still in another embodiment of the present invention, the material of which the yarn is made may be carbon fibers having a continuous thin coat of a polymer. Also, the carbon fibers may be replaced with glass fibers, silicon carbide fibers, aluminum oxide fibers, or any other structural fibers. Also, the matrix material may be a metal. In the case of a metal matrix, the fibers which become the matrix material may be titanium, a titanium alloy, or another metal material suitable as a matrix material.

In the preferred embodiment, the length of yarn, Ultrapek PEKEKK, is placed in an acetone bath for cleaning as indicated in step 104. Also in step 104, the yarn is randomized. The yarn is randomized by causing the fibers of the yarn to interlock, intertwine, and tangle with each other and by causing each fiber of the yarn to interlock, intertwine and tangle with itself. Preferably, the step of randomizing is performed by hooking the yarn with a stainless steel hook on the end of a rod and moving the hook through the yarn. The time required to randomize the yarn is reduced by spreading of the yarn as it is unspooled.

The yarn is soaked in the acetone bath for twenty minutes during which time the yarn is being randomized. The acetone bath is in a tank constructed for the purpose of ultrasonic cleaning material placed in the tank and the yarn is ultrasonically cleaned as it is being randomized in the acetone bath. Examples of such tanks are the cleaning tanks manufactured by the J. M. Ney Company, Bloomfield, Conn. The cleaning tanks are available in various liquid capacities. A controller controls a cleaning tank to ultrasonically clean material placed in the cleaning tank. Examples of such controllers are the 100, 200, 250, and 300 Series Cleaning Controllers also manufactured by the J. M. Ney Company.

The yarn is then removed from the acetone bath and placed in a bath of distilled water. The bath of distilled water is also in a tank constructed for the purpose of ultrasonic cleaning material placed in the tank. In step 106, the yarn placed in the bath of distilled water is ultrasonically cleaned in the bath of distilled water for twenty minutes during which time the yarn is again being randomized with a stainless steel hook as when the yarn was in the acetone bath.

After the yarn is randomized, the fibers which are to become the matrix material and the reinforcing fibers have become tangled, intertwined, and interlocked with each other. Each fiber is also tangled, intertwined, and interlocked with itself as well as with the other fibers. The tangled, intertwined, and interlocked fibers extend randomly in different directions throughout the mass of randomized yarn.

In step 108, the cleaned yarn is placed in a stainless steel pan which, in turn, is placed in a drying oven at 240° F. The cleaned yarn is dried for at least 48 hours. The drying of the cleaned yarn should be sufficient to remove all of the water content to prevent formation of bubbles later in the processing of the randomized yarn. In step 110, the dried yarn is manually bunched into an approximately six inch cubic block (preform) 40 shown schematically in FIG. 2. In FIG. 2, only two fibers 42, 44 illustrated. However, the preform 40 is totally made of fibers which fibers are made of either polymer or carbon.

In step 112, the preform is positioned in a compression mold. Sheets of polyimide film are then placed above and below the material in the mold as indicated in step 114. In step 116, the mold is placed into a hydraulic press and the material in the mold is heated to 800° F. while the material in the mold is under 2,000 pounds pressure (56 psi) and under a vacuum of about 29 inches of mercury. The degree of vacuum is such as to remove moisture from the material in the mold, to reduce the oxygen content in the material in the mold, and to eliminate volatiles from the material in the mold. In step 118, a pressure of 5,000 pounds (139 psi) is applied for fifteen minutes to the material in the mold while the material is maintained at 800° F. and under the vacuum. The pressure applied to the material in the mold is then increased to 108,000 pounds (3,000 psi) as indicated in step 120 while the material is maintained at 800° F. and under the vacuum. After the displacement reading of the pressure applied to the material in the mold stabilizes at 108,000 pounds (3,000 psi), one hour dwell time is allowed to pass as indicated in step 122 with the material at 800° F. and under the vacuum. Thus, the material in the mold is subjected to 3,000 psi and 800° F. for at least one hour.

While under 108,000 pounds pressure (3,000 psi) and under the vacuum, the material in the mold is cooled. In step 124, the material in the mold is air cooled for approximately four minutes. The material in the mold is then cooled to approximately 525° F. by a water mist which flows through the platens of the hydraulic press as indicated in step 126. After the material in the mold has cooled to 525° F., cooling is stopped and the temperature of the material in the mold is maintained at this temperature for thirty minutes as indicated in step 128. As indicated in step 130, water mist cooling of the material in the mold is resumed until the temperature of the material reaches 250° F. The material in the mold is then cooled with water until the temperature of the material in the mold reaches 100° F. as indicated in step 132. When the temperature of the material in the mold reaches 100° F., the vacuum is removed and the mold is removed from the press as indicated in step 133.

In step 134, a back plate of the mold is removed and the mold is turned upside down. The material in the mold is forced out of the mold using a hydraulic press as indicated in step 136. The polyimide films facilitate separation of the material from the mold. The edges of the material are then filed to remove any flash as indicated in step 138.

By compressing the randomized yarn in the mold and heating it in the manner described above, the polymer fibers melt but the carbon fibers do not melt. The melted polymer fibers form a matrix material and the carbon fibers are tangled, intertwined, and interlocked together throughout the matrix material. The matrix material and carbon fibers form a composite block 50

(see FIG. 3). The composite block 50 is a fiber reinforced composite structure.

Preferably, the mass of the composite block 50 is 591 grams and the thickness of the composite block 50 is sixteen millimeters. The carbon fiber content is preferably 68 percent by weight of the composite block 50 and the matrix material is preferably 32 percent by weight of the composite block 50. The proportion by weight of the carbon fibers in the composite block 50 is in the range of 50 to 70 percent. The proportion by weight of the matrix material in the composite block 50 is in the range of 30 to 50 percent.

While the composite block 50 is being made, the material in the mold is consolidated in only one direction. The consolidation of the material in the mold in only one direction results in a composite structure in which the majority of reinforcing carbon fibers lie substantially parallel to a plane extending in X and Y directions (perpendicular to the direction of consolidation) and portions of the reinforcing fibers lie transverse to the plane and weave through the X-Y plane in a Z direction. The fiber portions of each reinforcing carbon fiber tangle, intertwine, and interlock with the fiber portions of the other reinforcing fibers. Also, each reinforcing carbon fiber tangles, intertwines, and interlocks with itself. FIG. 3 illustrates only two reinforcing fibers 51, 54 in the composite block 50. However, the composite block 50 contains a substantial number of reinforcing fibers.

Each of the reinforcing carbon fibers extends continuously and randomly throughout the matrix material formed from the melted polymer fibers. The carbon fibers tangle, intertwine, and interlock with other carbon fibers and with themselves. Thus, substantial fiber reinforcement of the composite block 50 is provided in the X-Y plane as well as in the Z direction.

The composite block 50 can be made into a variety of products. As an example, as illustrated in FIG. 4, the composite block 50 is used to make a vertebral prosthetic spinal implant device 10 which is insertable into channels in adjacent faces of adjacent vertebrae. The implant device 10 supports the vertebrae and replaces an excised human disc. The human disc is excised to remove damaged and herniated tissue. The composite block 50 is cut into pieces and the pieces are machined to form the implant device 10.

The implant device 10 comprises a body insertable into channels formed in adjacent faces of adjacent vertebrae. The body includes serrated teeth 11 for engaging parts of the vertebrae. The serrated teeth 11 lock the implant device 10 in position at a prepared location.

The prosthetic implant device 10 of FIG. 4 is typically implanted between adjacent vertebrae to support and fuse together adjacent vertebrae in a spinal column to thereby treat or prevent back pain in patients with ruptured or degenerated intervertebral discs. The implant device 10 may be in a variety of shapes such as a cylindrical rod, or as shown in FIG. 4.

The implant device 10 has a vertical slot 52 extending through the top and bottom of the implant device 10. The vertical slot 52 is intersected centrally by a horizontal slot 53 extending through the sides of the implant device 10. The slots 52 and 53 provide cavities in the implant device 10 which are filled with bone implant. This bone material housed in the implant device 10 will grow out of the slots 52 and 53 and into the bone tissue of the adjoining vertebrae.

From the above description of the invention, those skilled in the art will perceive improvements, changes and modifications to the present invention. Such improvements, changes and modifications within the skill of the art are intended to be covered by the appended claims.

Having described the invention, the following is claimed:

1. A method of forming a fiber reinforced composite structure comprising the steps of:
    providing one-piece of yarn having a length and two ends and made of a plurality of continuous reinforcing fibers and other material which other material is to become a matrix, each of the plurality of reinforcing fibers having a length equal to the length of the one piece of yarn;
    randomizing the reinforcing fibers and the other material to extend randomly in substantially equal proportion in three dimensions throughout a mass of the yarn to intertwine and interlock the reinforcing fibers and the other material;
    forming the randomized yarn into a preform;
    consolidating the preform in a Z direction which is perpendicular to X and Y directions and causing a majority proportion of the reinforcing fibers to lie randomly in substantially two dimensions defined by a plane extending in X and Y directions and a minority proportion of the reinforcing fibers to weave through the plane in the Z direction; and
    melting the other material to form a matrix containing the continuous reinforcing fibers extending randomly in X, Y and Z directions throughout the matrix and have a length equal to the length of the one piece of yarn.

2. A method as set forth in claim 1 wherein the continuous reinforcing fibers include at least one of carbon fiber, glass fiber, silicon carbide fiber, aluminum oxide fiber and combinations thereof and the other material includes at least one of a polymer, a metal and a combination thereof.

3. A method as set forth in claim 2 wherein the continuous reinforcing fibers comprise carbon fibers and the other material comprises polymer fibers, each of the carbon fibers and the polymer fibers having a length equal to the length of the yarn.

4. A method as set forth in claim 2 wherein the other material comprises a metal including titanium.

5. A method as set forth in claim 1 wherein the continuous reinforcing fibers are carbon fibers and the other material comprises polymer particles bonded to the carbon fibers.

6. A method as set forth in claim 1 wherein the continuous reinforcing fibers are carbon fibers and the other material is a coating of polymer on the carbon fibers.

7. A method as set forth in claim 1 wherein said step on randomizing the yarn includes hooking the yarn with a hook and moving the hook through the yarn.

8. A method as set forth in claim 7 further including a step of cleaning the yarn during said step of randomizing the yarn.

9. A method as set forth in claim 1 further including a step of spreading the yarn before said step of randomizing.

10. A method as set forth in claim 1 wherein said step of consolidating includes compression molding the preform at a temperature of about 800° F.

11. A method as set forth in claim 1 further includng cooling the matrix and, subsequent to cooling the matrix, shaping the structure.

12. A method as set forth in claim 11 wherein said step of shaping the structure includes cutting the structure to form a prosthetic implant device.

13. A method as set forth in claim 12 wherein said step of cutting the structure includes cutting a plurality of serrated teeth and an aperture extending into the structure.

14. A method of forming a fiber reinforced composite structure comprising the steps of:
providing a yarn made of a plurality of continuous reinforcing fibers and other materials which is to become a matrix;
randomizing the yarn by hooking the yarn with a hook and moving the hook through the yarn;
forming the randomized yarn into a preform;
consolidating the preform in one direction; and
melting the other material to form a matrix containing the continuous reinforcing fibers which are randomized throughout the matrix.

15. A method as set forth in claim 14 further including a step of cleaning the yarn during said step of randomizing the yarn.

16. A method as set forth in claim 15 wherein said step of cleaning the yarn includes soaking the yarn in a bath of acetone; removing the randomized yarn; and soaking the randomized yarn in a bath of distilled water.

17. A method as set forth in claim 14 wherein a majority of the reinforcing fibers lie randomly and substantially parallel with a plane extending in X and Y directions and portions of the reinforcing fibers weave through the plane in a Z direction.

* * * * *